(12) United States Patent
Komann et al.

(10) Patent No.: US 11,826,500 B2
(45) Date of Patent: Nov. 28, 2023

(54) ARRANGEMENT COMPRISING A HOLDING DEVICE AND A PLURALITY OF CONTAINERS WITH A PARTICLE LOAD AFTER A TRANSPORT SIMULATION

(71) Applicant: SCHOTT Schweiz AG, St. Gallen (CH)

(72) Inventors: Christian Komann, Speicher (CH); Nina Krautwurst, St. Gallen (CH)

(73) Assignee: SCHOTT Schweiz AG, St. Gallen (CH)

(*) Notice: Subject to any disclaimer, the term of this patent is extended or adjusted under 35 U.S.C. 154(b) by 82 days.

(21) Appl. No.: 17/483,332

(22) Filed: Sep. 23, 2021

(65) Prior Publication Data

US 2022/0096732 A1  Mar. 31, 2022

(30) Foreign Application Priority Data

Sep. 25, 2020 (EP) ..................................... 20198369

(51) Int. Cl.
*A61M 5/00* (2006.01)
*B65B 57/00* (2006.01)
(Continued)

(52) U.S. Cl.
CPC .............. *A61M 5/002* (2013.01); *B65B 57/00* (2013.01); *B65D 25/108* (2013.01); *B65D 77/003* (2013.01); *B65D 77/2024* (2013.01)

(58) Field of Classification Search
CPC ...... A61M 5/002; B65B 57/00; B65D 25/108; B65D 77/003; B65D 77/2024
(Continued)

(56) References Cited

U.S. PATENT DOCUMENTS 5,950,832 A     9/1999  Perlman
2014/0311617 A1* 10/2014  Py ......................... A61J 1/1425
                                                    141/89
(Continued)

FOREIGN PATENT DOCUMENTS

EP         3 381 828 A1    10/2018

OTHER PUBLICATIONS

European Search Report dated Apr. 6, 2022 for European Patent Application No. 20198369.9 (4 pages).
(Continued)

*Primary Examiner* — Jacob K Ackun
(74) *Attorney, Agent, or Firm* — Taylor IP, P.C.

(57) ABSTRACT

An arrangement includes: a holding device including holding elements; and containers, each of the containers including a container wall which at least partially surrounds a container interior. The container wall has an exterior surface which faces away from the container interior. Each of the containers is detachably held by at least one of the holding elements by contact of the at least one holding element to the exterior surface of the container wall of the respective container. Directly after the arrangement has been subjected to a transport simulation, a number of particles of a particle size of at least 5 μm on the exterior surfaces of the containers does not exceed 2.7 particles per cm² of a sum of surface areas of the exterior surfaces of all the containers, the transport simulation consisting of a rotational flat drop test and a random vibration test which are conducted in that order.

19 Claims, 17 Drawing Sheets

(51) Int. Cl.
    *B65D 25/10*    (2006.01)
    *B65D 77/00*    (2006.01)
    *B65D 77/20*    (2006.01)

(58) Field of Classification Search
    USPC ......................................................... 206/364
    See application file for complete search history.

(56) References Cited

U.S. PATENT DOCUMENTS

| | | |
|---|---|---|
| 2018/0208377 A1 | 7/2018 | Kloke et al. |
| 2020/0156824 A1 | 5/2020 | Komann et al. |
| 2020/0297919 A1* | 9/2020 | Hemminger ............ A61L 2/206 |
| 2020/0407142 A1* | 12/2020 | Wolf ...................... B32B 27/08 |
| 2021/0212897 A1* | 7/2021 | Kloke .................... C08K 3/346 |
| 2022/0097914 A1* | 3/2022 | Küçük ..................... B01L 9/06 |

OTHER PUBLICATIONS

European Office Action dated Apr. 16, 2022 for European Patent Application No. 20 198 369.9 (5 pages).
European Search Report dated Apr. 6, 2021 for European Patent Application No. 20198369.9 (4 pages).

\* cited by examiner

100

103

100

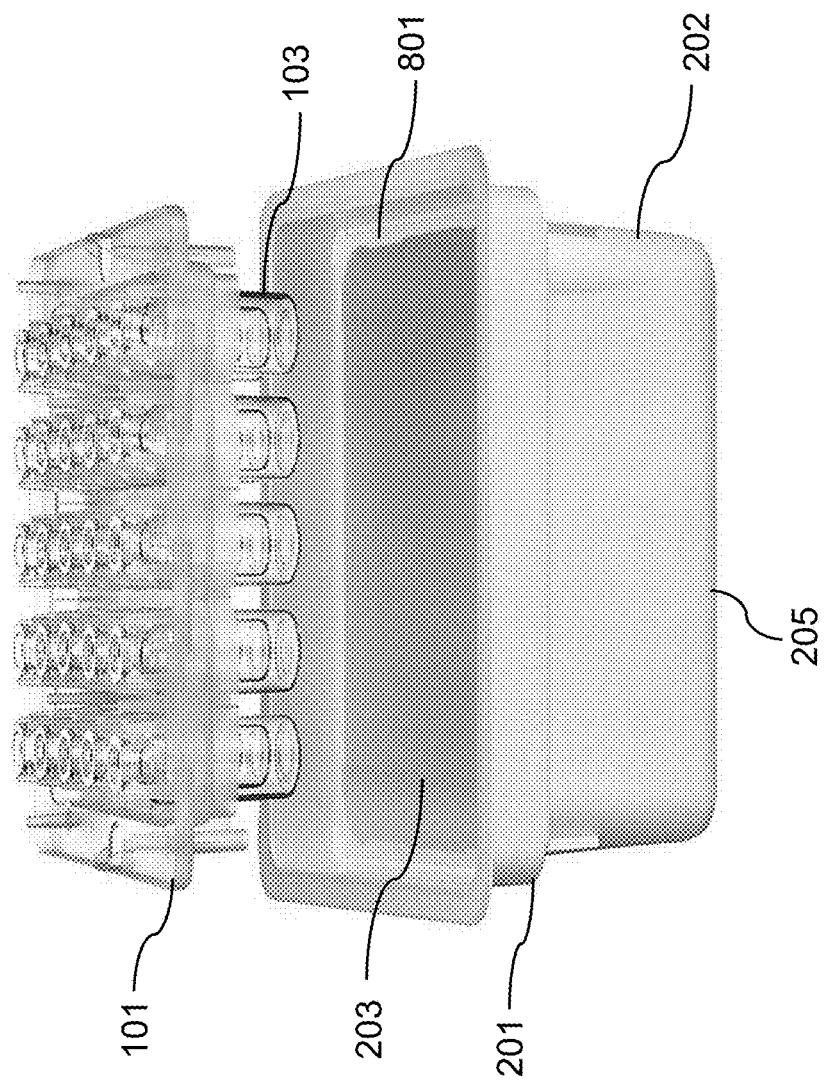

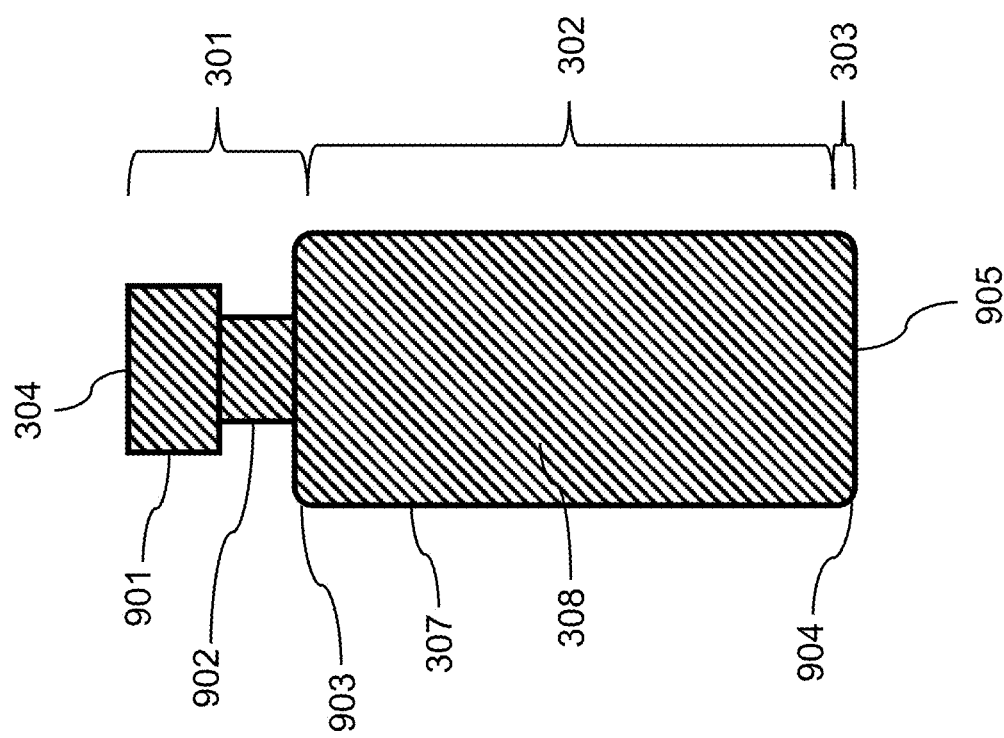

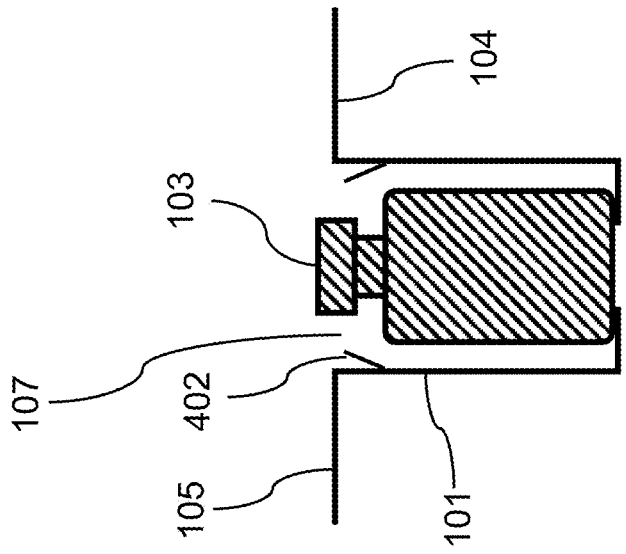
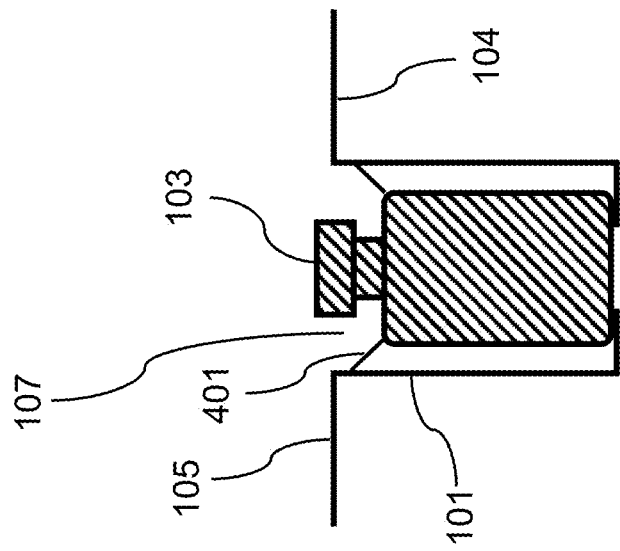

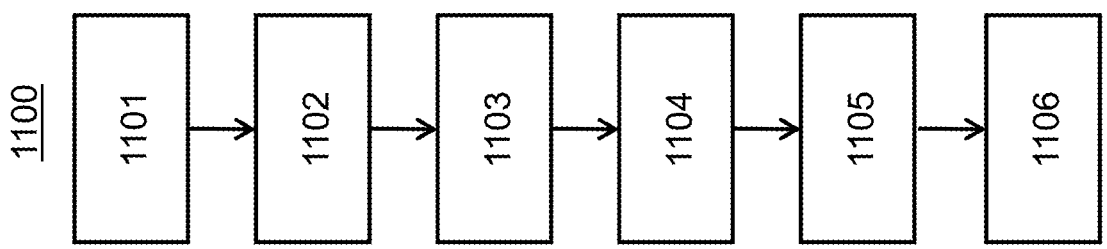

1200

1300

1400

ARRANGEMENT COMPRISING A HOLDING DEVICE AND A PLURALITY OF CONTAINERS WITH A PARTICLE LOAD AFTER A TRANSPORT SIMULATION

CROSS REFERENCE TO RELATED APPLICATIONS

This application claims priority to European Patent Application No. EP 20198369.9 filed on Sep. 25, 2020, which is incorporated in its entirety herein by reference.

BACKGROUND OF THE INVENTION

1. Field of the Invention

The present invention relates to an arrangement including a holding device, which comprises a plurality of holding elements, and a plurality of containers. Further, the invention relates to a process for preparing the arrangement; to a process which includes filling at least part of the containers with a pharmaceutical composition, or a cosmetical composition, or both; to a process which includes subjecting an arrangement to a transport simulation and determining a number of particles; and to uses of the arrangement; and of a filling machine.

2. Description of the Related Art

Containers made from glass and later on also from polymer have been applied for transporting fluids and powders safely for a long time. In the last decades, the arts in which glass and polymer containers are used for transporting fluids and powders have become increasingly diverse and sophisticated. One such art is the technical field of the present application: pharmaceutical packaging. In the pharmaceutical industry, containers—such as vials, syringes, ampoules and cartridges—are applied as primary packaging for all kinds of pharmaceutically relevant compositions, in particular drugs, such as vaccines, and also for cosmetical compositions, in particular cosmetical compositions which are to be injected into the skin.

In the processing of containers for use in pharmaceutical or cosmetical applications, generally so-called nested solutions are preferred nowadays, where a holding structure for containers (also referred to as nest) is used for concurrently holding or supporting a plurality of containers in a given configuration. The nests are usually delivered to a customer, such as a pharmaceutical company or filler, packaged in a transport or packaging container (also referred to as tub). For further processing the containers, the tubs are opened. Further processing the containers often includes automated steps of removing the containers from the tub; filling the containers with a composition, e.g. a pharmaceutical or cosmetical composition; closing the pre-filled containers, e.g. in case of syringes by applying a hypodermic needle via a Luer taper; and vacuum packaging individual containers in thin foil bags for retail. Each of the pre-ceding steps bears a risk of failures, such as processing failures, failures in failures in the connection between syringe and needle, and damages to the foil bags.

What is needed in art is a way to at least partly overcome a disadvantage arising from the prior art. What is also needed in the art is a way to provide an arrangement of a nested plurality of pharmaceutical or cosmetical packaging containers, which allows for further processing the containers after transport and storage with less processing failures. What is also needed in the art is an arrangement of a nested plurality of pharmaceutical or cosmetical packaging containers is provided which allows for less discharge failures after transport and storage of the arrangement and subsequent filling and closing of the containers. What is also needed in the art is an arrangement of a nested plurality of pharmaceutical or cosmetical packaging containers, which, after transport and storage of the arrangement, allows for less damages to a vacuum foil bag packaging. What is also needed in the art is a process for distinguishing an arrangement which solves one or more of the above problems from an arrangement which does not for quality control.

SUMMARY OF THE INVENTION

In some exemplary embodiments provided according to the invention, an arrangement includes a holding device including a plurality of holding elements and a plurality of containers. Each of the containers of the plurality of containers includes a container wall which at least partially surrounds a container interior. The container wall has an exterior surface which faces away from the container interior. Each of the containers of the plurality of containers is detachably held by at least one of the holding elements by contact of the at least one holding element to the exterior surface of the container wall of the respective container of the plurality of containers. Directly after the arrangement has been subjected to a transport simulation, a number of particles of a particle size of at least 5 μm on the exterior surfaces of the containers of the plurality of containers does not exceed 2.7 particles per $cm^2$ of a sum of surface areas of the exterior surfaces of all the containers of the plurality of containers. The transport simulation consists of a rotational flat drop test and a random vibration test which are conducted subsequently in that order.

In some exemplary embodiments provided according to the invention, a process includes: providing an arrangement including a holding device including a plurality of holding elements and a plurality of containers, each of the containers of the plurality of containers including a container wall which at least partially surrounds a container interior, the container wall having an exterior surface which faces away from the container interior, each of the containers of the plurality of containers being detachably held by at least one of the holding elements by contact of the at least one holding element to the exterior surface of the container wall of the respective container of the plurality of containers; subjecting the arrangement to a transport simulation; determining, for at least part of the containers of the plurality of containers, whether a number of particles on the exterior surfaces of the container walls of the at least part of the containers is above a threshold; and discarding the containers if the number of particles is above the threshold or filling at least part of the containers of the plurality of containers with a pharmaceutical composition, a cosmetical composition, or both if the number of particles is not above the threshold.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 8 illustrates a scheme of a further arrangement provided according to the invention with a holding device and containers taken out of a packaging container;

FIG. 9 illustrates a scheme of a container of an arrangement provided according to the invention;

FIGS. 10A and 10B illustrate schemes of a detail of the arrangement of FIG. 7 in cross-sectional view;

FIG. 11 illustrates a flow chart of a process provided according to the invention for preparing an arrangement provided according to the invention;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
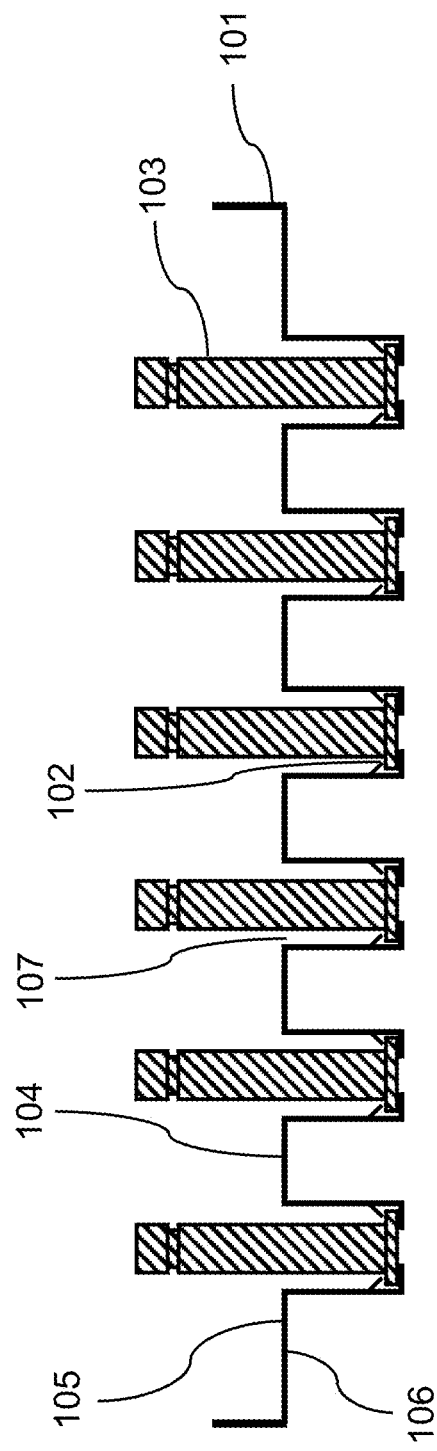
FIG. 1 illustrates a scheme of an arrangement provided according to the invention in cross-sectional view.

In some exemplary embodiments provided according to the invention, an arrangement includes a holding device, which includes a plurality of holding elements, and a plurality of containers. Each of the containers of the plurality of containers includes a container wall which at least partially surrounds a container interior. The container wall has an exterior surface which faces away from the container interior. Each of the containers of the plurality of containers is detachably held by at least one of the holding elements by contact of the at least one holding element to the exterior surface of the container wall of the respective container of the plurality of containers. Directly after the arrangement has been subjected to a transport simulation, a number of particles of a particle size of at least 5 µm on the exterior surfaces of the containers of the plurality of containers does not exceed 2.7 particles, such as 2.6 particles, 2.5 particles, 2.4 particles, 2.3 particles, 2.2 particles, 2.1 particles, 2.0 particles, 1.9 particles, 1.8 particles, 1.7 particles, 1.6 particles, or 1.5 particles, in each case per $cm^2$ of the sum of the surface areas of the exterior surfaces of all the containers of the plurality of containers. The transport simulation consists of a rotational flat drop test and a random vibration test which are conducted subsequently in that order. The transport simulation is described in more detail further herein in the test methods section.

In some embodiments, directly after the arrangement has been subjected to the transport simulation, a number of particles of a particle size of at least 2 µm on the exterior surfaces of the containers of the plurality of containers does not exceed 8.7 particles, such as 8.5 particles, 8.3 particles, 8.1 particles, 7.9 particles, 7.7 particles, 7.5 particles, 7.3 particles, 7.1 particles, 6.9 particles, 6.7 particles, 6.5 particles, 6.3 particles, 6.1 particles, 5.9 particles, 5.7 particles, 5.5 particles, 5.3 particles, 5.1 particles, 4.9 particles, 4.7 particles, or 4.5 particles, in each case per $cm^2$ of the sum of the surface areas of the exterior surfaces of all the containers of the plurality of containers.

In some embodiments, the plurality of containers consists of 4 to 500, such as 9 to 400, 12 to 300, 16 to 200, 16 to 160, 16 to 100, 16 to 90, 16 to 80, 16 to 70, 16 to 60, or 16 to 50, containers.

In some embodiments, the holding device includes at least one base body, the at least one base body may comprise the holding elements, or the holding elements of the plurality of holding elements are arranged at the at least one base body.

In some embodiments, the at least one base body includes a plurality of orifices in a first surface. Each of the containers of the plurality of containers extends at least through the first surface into an orifice of the plurality of orifices. In some embodiments, the first surface extends in directions of a width and a length of the base body.

In some embodiments, the at least one base body includes a further surface which is opposite to the first surface. Each orifice of the plurality of orifices extends from the first surface to the further surface. In some embodiments, the further surface extends in directions of a width and a length of the base body.

In some embodiments, each of the holding elements includes at least one of the orifices of the plurality of orifices, or the holding elements are different from the orifices of the plurality of orifices.

In some embodiments, each of the containers of the plurality of containers is, for example non-destructively, detachably held by a positive fit, or a frictional fit, or a combination of both of at least one holding element and the exterior surface of the container wall of the respective container of the plurality of containers. A container is non-destructively detachably held by one or more holding elements if the container can be withdrawn from the holding device without damaging the container and, for example, also without damaging the holding device. An exemplary positive fit is a positive fit with a first end part or further end part or both of a container. In some embodiments, the holding elements are designed and arranged such that establishing the positive fit includes elastically deforming the respective one or more holding elements. Here, the one or more holding elements may remain elastically deformed once the positive fit has been established or not.

In some embodiments, the positive fit, or the frictional fit, or the combination of both, upon a force, which is 2 times an empty weight force of the container, being exerted to the container in a direction, prevents any movement of the container in this direction by more than 5%, such as by more than 3% or by more than 1%, in each case of an extent of the container in this direction.

In some embodiments, the at least one base body is at least partially, for example completely, plate-shaped.

In some embodiments, the first surface is a planar surface. Additionally or alternatively, the further surface may be a planar surface. In some embodiments, the first and further surfaces are plan-parallel to one another.

In some embodiments, the arrangement further includes a, for example closed, packaging container. The packaging container includes, for example consists of, a packaging container wall, which at least partially surrounds a packaging container interior. The holding device and the containers are arranged in the packaging container interior.

In some embodiments, the packaging container is closed by a lid which is joined to the packaging container. An exemplary lid is a multi-layer sheet. Additionally or alternatively, the lid may be gas-permeable.

In some embodiments, the packaging container wall comprises, for example consists of, a packaging container polymer.

In some embodiments, the packaging container polymer is one selected from the group consisting of a polycondensation polymer, such as polyethylene terephthalate; a polyacrylate, such as polymethylmethacrylate; and a polyolefin, such as polypropylene or polyethylene; or a combination of at least two thereof.

In some embodiments, the arrangement further includes a, for example closed, outer packaging. The packaging container is arranged in the outer packaging. An exemplary outer packaging is a pouch, for example made from a plastic film. Additionally or alternatively, the outer packaging may provide a barrier against a permeation of an inert gas. Additionally or alternatively, the outer packaging may be hermetically sealed. Additionally or alternatively, the outer packaging may be less permeable for the inert gas than the lid. In some embodiments, the outer packing provides a barrier action against a permeation of the inert gas, whereas the lid is permeable for the inert gas.

In some embodiments, the outer packaging comprises an atmosphere, which comprises an inert gas at a proportion of at least 50 vol.-%, such as at least 60 vol.-%, at least 70 vol.-%, at least 80 vol.-%, at least 90 vol.-%, or at least 95 vol.-%, in each case based on a volume of the atmosphere.

In some embodiments, the containers have been decontaminated, for example sterilized. In some embodiments, the arrangement has been decontaminated, for example sterilized. In the context of the present application, decontamination is defined as an umbrella term for reducing the amount of microbes and biological agents, such as fungi, bacteria, viruses, spore forms, prions, unicellular eukaryotic organisms, etc. The special terms disinfection and sterilization differ in the amount of reduction of these. While disinfection only reduces the amount of said contaminants, sterilization effectively kills, deactivates, or eliminates all forms of life and other biological agents which are present, i.e. a reduction of 100%. Hence, disinfection is less effective than sterilization.

In some embodiments, the containers of the plurality of containers are packaging containers for a pharmaceutical or cosmetical packaging good or both. In some embodiments, the containers of the plurality of containers are primary packaging containers for a pharmaceutical composition or a cosmetical composition or both. An exemplary pharmaceutical composition is a liquid. An exemplary cosmetical composition is a liquid. In some embodiments, the containers of the plurality of containers are suitable for packaging parenteralia in accordance with section 3.2.1 of the European Pharmacopoeia, $7^{th}$ edition from 2011.

In some embodiments, each of the containers of the plurality of containers includes, in the following sequence, for example from top to bottom,
   a. a first end part, comprising a discharge orifice,
   b. a body part, and
   c. a further end part.

In some embodiments, the body part is of cylindrical shape. In case of a container which is a syringe, the body part of cylindrical shape is often referred to as barrel.

In some embodiments, the further end part is a standing base, or comprises a further orifice, or both. An exemplary container, the further end part of which is a standing base, is a vial or a cartridge. An exemplary container, the further end part of which comprises a further orifice is a syringe. In some embodiments, the discharge orifice of a container has an orifice area which is less than an orifice area of the further orifice of the same container. An exemplary further orifice is designed to accommodate a plunger.

In some embodiments, for each of the containers of the plurality of containers, an area of the further orifice is more than an area of the discharge orifice.

In some embodiments, the further end part further includes a rim which projects laterally from beyond the body part and at least partially, for example fully, hems the further orifice.

In some embodiments, the further end parts of the containers of the plurality of containers face a bottom of the packaging container, herein also referred to as packaging container bottom.

In some embodiments, for each of the containers of the plurality of containers, the first end part includes a connecting element. The connecting element includes a thread for connecting an auxiliary part to the respective container of the plurality of containers. An exemplary auxiliary part is one selected from the group consisting of a needle, a nozzle, and a tubing, or a combination of at least two therefore. An exemplary needle is a hypodermic needle.

In some embodiments, for each of the containers of the plurality of containers, the first end part includes a male part of a taper fitting. An exemplary taper fitting is a Luer taper. Generally, the Luer taper may comprise a thread or not.

In some embodiments, the male part of the taper fitting comprises a thread. In some embodiments, the thread is arranged in a sleeve.

In some embodiments, for each of the containers, throughout the body part a thickness of the container wall is in a range from ±0.3 mm, such as ±0.2 mm, ±0.15 mm, ±0.1 mm, or ±0.08 mm, in each case based on a mean value of the thickness of the container wall in the body part of the respective container of the plurality of containers.

In some embodiments, for each of the containers of the plurality of containers, throughout the body part a thickness of the container wall is in a range from 0.2 to 3 mm, such as from 0.3 to 2.5 mm or from 0.4 to 2.2 mm. In an exemplary embodiment, for each of the primary packaging containers, throughout the body part a thickness of a container wall is in a range from 1.0 to 1.1 mm. In a further exemplary embodiment, for each of the primary packaging containers, throughout the body part a thickness of a container wall is in a range from 1.4 to 1.8 mm. In yet a further exemplary embodiment, for each of the primary packaging containers, throughout the body part a thickness of a container wall is in a range from 0.6 to 2.0 mm.

In some embodiments, for each of the containers of the plurality of containers, a volume of the container interior is in a range from 0.5 to 100 mL, such as from 1 to 100 mL, from 1 to 50 mL, from 1 to 10 mL, or from 2 to 10 mL.

In some embodiments, the containers of the plurality of containers are selected from the group consisting of vials, syringes, cartridges, and ampoules, or a combination of at least two thereof. An exemplary cartridge is designed for being used as a reservoir in a, for example portable, medical device. An exemplary portable medical device is an insulin pump.

In some embodiments, for each of the containers of the plurality of containers, the container wall comprises, for example consists of, a glass, or a polymer, or both.

In some embodiments, the polymer is a cyclic olefin copolymer, or a cycloolefin polymer, or a mixture thereof.

In some embodiments, the glass is of a type selected from the group consisting of a borosilicate glass, for example a type I glass; an aluminosilicate glass; and fused silica; or of a combination of at least two thereof.

In some embodiments, the glass has a content of alkali metal atoms and alkali metal ions of in sum at least 1 wt.-%, such as at least 2 wt.-%, at least 3 wt.-%, at least 4 wt.-%, or at least 5 wt.-%, in each case based on the weight of the glass. Typically, the content of alkali metal atoms and alkali metal ions is in sum not more than 20 wt.-%, such as not more than 15 wt.-%, in each case based on the weight of the glass.

In some exemplary embodiments provided according to the invention, a process for preparing the previously described arrangement provided according to the invention is provided. The process including as process steps:

A) providing
  I) the holding device, and
  II) the plurality of containers;
B) loading the holding device with the containers of plurality of containers such that each of the containers of plurality of containers is, for example non-destructively, detachably held by at least one of the holding elements by contact of the at least one holding element to the exterior surface of the container wall of the respective container of plurality of containers.

In some embodiments, the process comprises as further process steps
  C) placing the holding device with the containers of plurality of containers into the packaging container, and
  D) closing the packaging container.

In some embodiments, the process step D) comprises joining a lid to the packaging container. An exemplary lid is a sheet. An exemplary sheet is a multilayer sheet. An exemplary lid is permeable for an inert gas. In some embodiments, the joining is effected by adhesively bonding or by sealing the lid to the packaging container. In the case of sealing, the joint is created by a liquid and its solidification. Here, a hotmelt may be used. In the case of adhesive bonding, chemical bonds which create the joint are formed between the interfaces or surfaces of the two articles to be joined.

In some embodiments, the process comprises as further process steps
  E) placing the packaging container with the holding device and the containers of plurality of containers into the outer packaging, and
  F) closing the outer packaging.

An exemplary outer packaging is a pouch, for example made from a plastic film. An exemplary process step F) comprises sealing the outer packaging. An exemplary outer packaging provides a barrier against a permeation of an inert gas. An exemplary outer packaging is hermetically sealed.

In some embodiments, prior to the process step F), an atmosphere in the outer packing is adjusted. In some embodiments, adjusting the atmosphere in the outer packing comprises introducing an inert gas into the outer packaging. In some embodiments, the outer packaging is less permeable for the inert gas than the lid. In some embodiments, the outer packing provides a barrier action against a permeation of the inert gas, whereas the lid is permeable for the inert gas.

In some embodiments, after the process step B), the process comprises a further process step, which comprises treating at least part of the exterior surface of at least part, for example of each, of the containers of plurality of containers. In some embodiments, the treating is conducted prior to the process step D), for example prior to the process step C).

In some embodiments, the treating comprises a lyophilisation.

In some exemplary embodiments provided according to the invention, a process comprises as process steps
  A. providing the previously described arrangement provided according to the invention;
  B. filling at least part, for example all, of the containers of plurality of containers with a pharmaceutical composition, or a cosmetical composition, or both.

In some embodiments, prior to the process step B., the packaging container is opened.

In some embodiments, prior to the process step B., the holding device is removed from the packaging container.

In some embodiments, in the process step B., the containers of the at least part of the containers are held by the holding device.

In some embodiments, in the process step B., each container of the at least part of the containers is filled via its discharge orifice.

In some embodiments, prior to the process step B., the outer packaging is opened and the packaging container is removed from the outer packaging.

In some embodiments, the process is a process for filling the containers of the at least part of the containers with the pharmaceutical composition, or the cosmetical composition, or both.

In some embodiments, in the process step B., at least one filled container is obtained and the process further comprises a process step
  C. connecting an auxiliary part to the at least one filled container, for example via a taper fitting or via a thread or both.

An exemplary auxiliary part is one selected from the group consisting of a needle, a nozzle, and a tubing, or a combination of at least two therefore. An exemplary needle is a hypodermic needle.

In some exemplary embodiments provided according to the invention, a process comprises as process steps
  A] providing an arrangement, including
    I] a holding device, which includes a plurality of holding elements, and
    II] a plurality of containers, each of the containers of the plurality of containers includes a container wall which at least partially surrounds a container interior, the container wall has an exterior surface which faces away from the container interior,
    each of the containers of the plurality of containers is, for example non-destructively, detachably held by at least one of the holding elements by contact of the at least one holding element to the exterior surface of the container wall of the respective container of the plurality of containers;

B] subjecting the arrangement to a transport simulation;

C] determining, for at least part, for example all, of the containers of the plurality of containers, whether a number of particles on the exterior surfaces of the container walls of the at least part of the containers is above a threshold; and D] if
 I] the number of particles is above the threshold: discarding the containers,
 II] the number of particles is not above the threshold: filling at least part of the containers with a pharmaceutical composition, or a cosmetical composition, or both.

As the transport simulation of process step B] any exposure to a mechanical stress or a deviation from an ambient temperature of 23° C., an ambient air pressure of 100 kPa (0.986 atm) or a relative atmospheric humidity of 50% which the skilled person deems suitable in the context of the invention comes into consideration. An exemplary mechanical stress is one selected from the group consisting of a vibration, a drop, an impact, and a loading with weight, for example from above, or a combination of at least two thereof. An exemplary transport simulation includes a simulation of one selected from the group consisting of a manual handling; a mechanical handling; a stacking; a rail switching; an environmental hazard, for example a temperature shock or increased moisture or both; a low ambient pressure or high-altitude hazard; or a combination of at least two thereof. An exemplary process is a process for filling the at least part of the containers with the pharmaceutical composition, or the cosmetical composition, or both. Exemplary containers of the plurality of containers are those specified in any of the embodiments of the arrangement provided according to the invention. Here, the holding elements of the holding device may be of any design which the skilled person deems suitable. In particular, the design of the holding elements is not limited to the holding elements described in the context of the arrangement provided according to the invention. The holding device, for example, has one or more features of the holding device of the arrangement provided according to the invention. In the context of the process provided according to the invention, the holding device is, however, not limited to the embodiments of the arrangement. Rather, in the process steps B] to D], it may be tested if the arrangement, provided in step A], is an arrangement provided according to the invention. Accordingly, the process may provide a method of separating arrangements provided according to the invention from those which are not provided according to the invention. In that sense, the process may be a process of providing the arrangement according to the invention. Therefore, the process shares the same inventive idea with the arrangement provided according to the invention.

An exemplary threshold is a number of particles of a particle size of at least 5 µm of 2.7 particles, such as 2.6 particles, 2.5 particles, 2.4 particles, 2.3 particles, 2.2 particles, 2.1 particles, 2.0 particles, 1.9 particles, 1.8 particles, 1.7 particles, 1.6 particles, or 1.5 particles, in each case per $cm^2$ of the sum of the surface areas of the exterior surfaces of the container walls of the at least part of the containers of the plurality of containers. A further exemplary threshold is a number of particles of a particle size of at least 2 µm of 8.7 particles, such as 8.5 particles, 8.3 particles, 8.1 particles, 7.9 particles, 7.7 particles, 7.5 particles, 7.3 particles, 7.1 particles, 6.9 particles, 6.7 particles, 6.5 particles, 6.3 particles, 6.1 particles, 5.9 particles, 5.7 particles, 5.5 particles, 5.3 particles, 5.1 particles, 4.9 particles, 4.7 particles, or 4.5 particles, in each case per $cm^2$ of the sum of the surface areas of the exterior surfaces of the container walls of the at least part of the containers of the plurality of containers.

In some embodiments, the transport simulation comprises one or more of the schedules A to J as specified in ASTM D4169-16. Additionally or alternatively, the transport simulation may comprise a rotational flat drop test or a random vibration test or both. An exemplary rotational flat drop test is described further herein in the test methods section. An exemplary random vibration test is described further herein in the test methods section.

In some embodiments, in the process step D]., at least one filled container is obtained and the process further comprises a process step D. connecting an auxiliary part to the at least one filled container, for example via a taper fitting or via a thread or both.

An exemplary auxiliary part is one selected from the group consisting of a needle, a nozzle, and a tubing, or a combination of at least two therefore. An exemplary needle is a hypodermic needle.

In some exemplary embodiments provided according to the invention, a use of the arrangement provided according to the invention for storage or transport of at least part of the containers of the plurality of containers is provided.

In some exemplary embodiments provided according to the invention, a use of a filling machine for filling at least part of the containers of the plurality of containers of the arrangement provided according to the invention with a pharmaceutical composition, or a cosmetical composition, or both is provided. Therein, the at least part of the containers of the plurality of containers may be held by the holding device as described in the context of the arrangement.

Features described as exemplary for any embodiments provided according to the invention, for example according to the arrangement, are analogously exemplary in other embodiments provided according to the invention.

Container

The container of the plurality of containers provided according to the invention may have any size or shape which the skilled person deems appropriate in the context of the invention. In some embodiments, a first end part of the container comprises a discharge orifice, which allows for discharging a pharmaceutical composition from the interior volume of the container. In that case, the wall of the container encloses the interior volume of the container only partially. The container is for example a glass container, a wall of glass (container wall) of which at least partially encloses an interior volume of the container. In some embodiments, the wall of glass is of a one-piece design. The wall of glass may be made by blow molding a glass melt; or by preparing a tube of a glass, for example in form of a hollow cylinder, forming the bottom of the container from one end of the tube, thereby closing the tube at this end, and forming the top region of the container from the opposite end of the tube. In some embodiments, the wall of glass is transparent. Alternatively, the container wall may be made from a polymer. In that case, the container wall may also be transparent.

For the use in this document, the interior volume represents the full volume of the interior of the container. This volume may be determined by filling the interior of the container with water up to the brim and measuring the volume of the amount of water which the interior can take up to the brim. Hence, the interior volume as used herein is not a nominal volume as it is often referred to in the technical field of pharmacy. This nominal volume may for example be less than the interior volume by a factor of about 0.5.

Glass

The container wall of each container of the plurality of containers comprises a glass, for example essentially consists of the glass. This glass may be any type of glass and may have any composition which the skilled person deems suitable in the context of the invention. In some embodiments, the glass is suitable for pharmaceutical packaging. In some embodiments, the glass is of type I in accordance with the definitions of glass types in section 3.2.1 of the European Pharmacopoeia, 7$^{th}$ edition from 2011. Additionally or alternatively to the preceding, the glass may be selected from the group consisting of a borosilicate glass, an aluminosilicate glass, and fused silica; or a combination of at least two thereof. For the use in this document, an aluminosilicate glass is a glass which has a content of $Al_2O_3$ of more than 8 wt.-%, such as more than 9 wt.-% or in a range from 9 to 20 wt.-%, in each case based on the total weight of the glass. An exemplary aluminosilicate glass has a content of $B_2O_3$ of less than 8 wt.-%, such as at maximum 7 wt.-% or in a range from 0 to 7 wt.-%, in each case based on the total weight of the glass. For the use in this document, a borosilicate glass is a glass which has a content of $B_2O_3$ of at least 1 wt.-%, such as at least 2 wt.-%, at least 3 wt.-%, at least 4 wt.-%, at least 5 wt.-%, or in a range from 5 to 15 wt.-%, in each case based on the total weight of the glass. An exemplary borosilicate glass has a content of $Al_2O_3$ of less than 7.5 wt.-%, such as less than 6.5 wt.-% or in a range from 0 to 5.5 wt.-%, in each case based on the total weight of the glass. In some embodiments, the borosilicate glass has a content of $Al_2O_3$ in a range from 3 to 7.5 wt.-%, for example in a range from 4 to 6 wt.-%, in each case based on the total weight of the glass.

A glass which is provided according to the invention may be essentially free from B. Therein, the wording "essentially free from B" refers to glasses which are free from B which has been added to the glass composition by purpose. This means that B may still be present as an impurity, but for example at a proportion of not more than 0.1 wt.-%, such as not more than 0.05 wt.-%, in each case based on the weight of the glass.

Holding Device

The holding device of the arrangement provided according to the invention may, generally, be any device which, for the skilled person, comes into consideration for holding the plurality of containers by the plurality of holding elements. An exemplary holding device has been prepared by deep drawing or injection molding. Additionally or alternatively, the holding device may be made from one or more plastics.

Base Body

The base body of the holding device may be of any shape or material which the skilled person deems appropriate in the context of the invention. In some embodiments, the base body is made from one or more plastics. Additionally or alternatively, the base body has a shore A hardness of at least 80, such as at least 90. Additionally or alternatively, the base body is of a plate-like shape. In some embodiments, a width and a length of the base body are each at least 3 times, such as at least 5 times, at least 10 times, or at least 20 times, a thickens of the base body. The plurality of orifices, for example, consists of 4 to 500, such as 9 to 400, 12 to 300, 16 to 200, 16 to 160, 16 to 100, 16 to 90, 16 to 80, 16 to 70, 16 to 60, or 16 to 50, orifices. Additionally or alternatively, the holding device provided according to the invention is, for example, configured for holding 4 to 500, such as 9 to 400, 12 to 300, 16 to 200, 16 to 160, 16 to 100, 16 to 90, 16 to 80, 16 to 70, 16 to 60, or 16 to 50, containers. Further, the orifices of the plurality of orifices in the first surface may be any kind of orifice which the skilled person deems appropriate to accommodate the containers such that they can be held by the holding elements. An exemplary orifice is a recess or a through-hole. An exemplary through-hole has a circular cross section. An exemplary through-hole is of a cylindrical shape. This means that a lateral surface of the through-hole is a cylinder shell surface. Additionally or alternatively, the orifices are arranged at the first surface in a regular pattern, for example in an array which consists of rows and columns which are, for example, perpendicular to one another.

Holding Elements

The holding elements of the holding device may, generally, be of any design which, for the skilled person, comes into consideration for holding the plurality of containers to the holding device. Exemplary holding elements have been manufactured in one piece with the base body, for example with the holding device. Additionally or alternatively, the holding elements are designed and arranged to hold the plurality of containers by a positive fit or by a frictional locking or by both. In some embodiments, the positive fit holds the containers against the gravitational force if the holding device is positioned upright. Additionally or alternatively, the holding elements are designed and arranged to essentially prevent any movement of the containers relative to the holding device during the vibration test. Additionally or alternatively, the holding elements are designed and arranged to assume a holding configuration and to hold the containers in this holding configuration; and to be transferred into a release configuration which is designed for withdrawing the containers from the holding device, and vice versa. In some embodiments, transferring the holding elements from the holding configuration to the release configuration and vice versa includes moving at least part of the holding elements relative to the base body. In some embodiments, in the holding configuration as well as in the release configuration, the holding elements are connected to the base body.

Pharmaceutical and Cosmetical Composition

In the context of the invention, every pharmaceutical composition and every cosmetical composition which the skilled person deems suitable comes into consideration. A pharmaceutical composition is a composition comprising at least one pharmaceutically active ingredient. An exemplary pharmaceutically active ingredient is a vaccine. A cosmetical composition is a composition comprising at least one cosmetically active ingredient. An exemplary cosmetically active ingredient is hyaluronic acid or botulinum toxin. The pharmaceutical or cosmetical composition may be fluid or solid or both. An exemplary solid composition is granular such as a powder, a multitude of tablets or a multitude of capsules. A further exemplary pharmaceutical or cosmetical composition is a parenterialium, i.e. a composition which is intended to be administered via the parenteral route, which may be any route which is not enteral. Parenteral administration can be performed by injection, e.g. using a needle (usually a hypodermic needle) and a syringe, or by the insertion of an indwelling catheter.

Test Methods

The following test methods are to be used in the context of the invention. Unless otherwise specified, the measurements have to be carried out at an ambient temperature of 23° C., an ambient air pressure of 100 kPa (0.986 atm) and a relative atmospheric humidity of 50%.

Transport Simulation

The transport simulation is conducted in accordance with ASTM D4169-16. In particular, the transport simulation consists of 2 sequences which are performed with the same sample one after the other. The environmental conditions in the test room are:
- temperature: in the range from 15 to 35° C.
- relative humidity: <85%
- air pressure: in the range from 860 to 1060 hPa Sample The sample is pallet unit which consists of a wooden pallet on which boxes of corrugated cardboard are stacked such that the overall dimensions of the sample are
- length: 1200 mm,
- width: 800 mm and
- height: 940 mm.

The boxes are tightly secured to each other by plastic stretch foil. Each of the boxes is filled with identical arrangements of the kind of arrangement to be tested. The boxes do not contain any additional filling material. Accordingly, each arrangement consists of a holding device which is fully loaded with identical empty containers.

First Sequence

The first sequence is conducted in accordance with schedule A—Mechanical Handling—Unitized Loads as described in section 10.3.2 of ASTM D4169-16. A rotational flat drop test in accordance with ASTM D6179, method C is conducted. The drop height is selected from the table in section 10.3.2.3 of ASTM D4169-16 based on the assurance level II. The test consists of 1 drop from each opposite base edge of the sample. One edge of the sample is supported by the floor. The other side is raised up to the drop height and released to fall flat on the impact surface (bottom of the wooden pallet). This procedure is performed with each opposite base edge which results in 4 drops altogether. The following test steps are performed:
1. Support edge 3-6 and raise edge 3-5; drop on face 3
2. Support edge 3-5 and raise edge 3-6 drop on face 3
3. Support edge 2-3 and raise edge 3-2; drop on face 3
4. Support edge 3-4 and raise edge 3-4; drop on face 3

If any of the boxes of the sample has moved one the pallet in one of the preceding steps 1. to 3., it is pushed back into place before the subsequent step. At the end of step 4, all boxes are pushed back to their original place on the pallet.

Second Sequence

The second sequence is conducted in accordance with schedule D—Stacked—Vibration as described in section 12.2 of ASTM D4169-16. A random vibration test in accordance with ASTM D4728 is conducted. In the test, the sample is in normal shipping orientation, i.e. with the wooden pallet at the bottom. The sample is loaded in accordance with section 11.4 of ASTM D4169-16. The top load TL is calculated from formula (3) as given in section 11.4 of ASTM D4169-16. Therein, H=2.7 m and F=1. Further parameters of the second sequence are:
- Truck Loop Profile:
- 0.40 $G_{rms}$ for 40 min
- 0.54 Grms for 15 min
- 0.70 Grms for 5 min
- Numbers of Loops: 1
- Duration in Total: 1 h on Face 3
- Air Profile:
- AL II/Grms: 1.05
- Test Duration: 2 h on Face 3

Particle Load after Transport Simulation

Directly after the sample has been subjected to the above transport simulation, the particle load of the exterior surfaces of the containers of the arrangement to be studied is determined in particles of a specific size range (particle class) per $cm^2$ of the sum of the surface areas of the exterior surfaces. Any further handling of the sample which could lead to the formation of further particles is to be avoided between the transport simulation and determination of the particle load.

Liquid Particle Counting System

The particle load of the containers of the arrangement to be studied is determined using a liquid particle counting system which includes a particle counter Pacific Scientific Hiac Royco, Model 9703 (F4-088) and a desktop computer on which runs the software PharmSpec 3.4.0 as it comes with the particle counter. Generally, the particle counter draws up the test liquid via an ascending pipe and guides it past a scattered light sensor. The signals coming from the scattered light sensor are read out and processed by the software. In this test method, only particle-free water which has been prepared by an H2O-EDI-2-T Arium® advance EDI (101/h) tabletop system from Sartorius AG, Göttingen, Germany is used for cleaning, for flushing and rinsing, as zero sample, for any filter exchange and for preparing the test liquid. This system is an apparatus for preparing pure water of type 2. The system has a flow performance of 10 liters per hour.

Preparation of the Particle Counter

The medium required for flushing (particle-free water) and testing (test liquid) is filled into the vessel at least 1 hour before the test. The particle counter is operated under laminar flow conditions. Prior to the start of the tests, the complete laminar flow workstation running with working flow is cleaned with a moistened particle-free cloth. The lifting arm to which the suction pipe is attached can be controlled via the control panel. Before the first measurement can be carried out, the sampler must be cleaned and adjusted so that the suction tube is immersed as deeply as possible in the test liquid without touching the bottom of the vessel. The adjustment is carried out with the vessel with which the later measurements are also carried out. The lowest position of the lifting arm is saved and then the lifting arm is moved back to the starting position. In order to clean the sampler, a vessel which has been flushed 3 times with particle-free water is filled with at least 35 mL of particle-free water and positioned under the lifting arm. The lifting arm is moved into the lower position which has been saved as described above. Again, the lifting arm must not touch the bottom of the vessel. The automatic flushing sequence is started. Per cleaning run 10 mL of liquid consumed. 4 cleaning runs are conducted. Under no circumstances should air be sucked in. Therefore, there must be at least 35 mL of particle-free water in the vessel. After cleaning, the lifting arm is moved to the upper position.

Zero Sample

Before starting the tests, the particle-free water used to prepare the test liquid must be checked for its particle content. For this purpose, the vessel which will be used for the measurements is rinsed 3 times with particle-free water. Then, the vessel is filled with 40 mL of the particle-free water as zero sample. After the zero sample has been left to stand for at least 2 minutes to deaerate, the test can be started. The particle counter measures the number of particles in a given volume of the particle-free water. Here, particles of all particle sizes possible have to be recorded. For this, the machine draws up and tests 6 times 5 mL of liquid. The first measurement is rejected. An acceptance criterion is set to a maximum of 25 particles of particle size of at least 10 µm per 25 mL of the particle-free water. If this value is not met, preparation of the particle-free water must be adapted and measurement of the zero sample must be repeated until the acceptance criterion is met.

Test Liquid

The stretch foil is removed from the cardboard boxes. The box which contains the arrangement to be studied is taken from the pallet and opened under laminar flow. All further steps are conducted under laminar flow. The arrangement to be studied is taken out of the box. A glass beaker with enough particle-free water for immersing one primary packaging container at a time to half of its length in the water in an upright orientation is prepared. In any case, a minimum of 40 mL of particle-free water is used and referred to as pool in the following. The glass beaker is flushed at least 3 times with particle-free water beforehand. All openings of the primary packaging containers of the arrangement to be studied are closed by stoppers which have been rinsed at least 3 times with particle-free water beforehand. One after the other, each of the primary packaging containers is immersed to half of its length in the pool (the same particle-free water) in an upright orientation and manually agitated to make a stirring motion while maintaining the upright orientation for 5 s. In the case of syringes, the upright orientation means that the tips of the syringes face upwards. The test liquid is the pool in which all the primary packaging containers of the arrangement have been washed as described in the preceding.

Measurement

The test liquid is filled into the vessel at least 1 hour before the test. The particle counter measures the number of particles of particle sizes of ≥2 µm, ≥5 µm, ≥10 µm, ≥15 µm, ≥25 µm, ≥50 µm, ≥75 µm and ≥100 µm. For this, the machine tests 6 times 5 mL of the test liquid and rejects the first measurement. Therefore, the minimum volume of the test liquid is 35 mL. For each of the above particle size classes, the number of particles per $cm^2$ is determined by dividing the number particles in the test liquid as determined by the particle counter by the sum of the area of the exterior surfaces of the primary packaging containers of the arrangement.

Wall Thickness and Tolerance of Wall Thickness

The wall thickness and deviations from the mean value of the wall thickness (tolerance) are determined in accordance with the following standards for the respective type of container:

DIN ISO 8362-1 for vials,
DIN ISO 9187-1 for ampoules,
DIN ISO 110 4 0-4 for syringes,
DIN ISO 13926-1 for cylindrical cartridges, and
DIN ISO 11040-1 for dental cartridges.

Discharge Failure

NPO Resistance

Herein, "NPO" stands for needle pop-off and denotes the abrupt detachment of a needle arrangement from a syringe body, in particular of a needle arrangement connected to the syringe body via a Luer lock connection. The NPO resistance indicates a threshold value of a force which, in the context of this test procedure, is applied to a plunger rod introduced into the syringe body and operatively connected to the latter. The NPO resistance is defined as the highest threshold value of a force, below which needle pop-off occurs in not more than 1.8% of the tested syringe bodies. At least 56 measurements of syringe bodies of the same configuration and design are needed in order to provide a meaningful result for the NPO resistance. At high pressure (triggered by force applied to the syringe body via the plunger rod), the needle arrangement may start to turn and come loose from the syringe body at high speed, i.e., the inner cone of the needle arrangement complementing the outer cone of the syringe body (Luer taper) may come loose, and, thus, the needle arrangement may detach from a syringe body.

Leakage Resistance

Herein, leakage stands for leakage that occurs between the syringe body and the needle arrangement as a result of the applied force and the acting pressure. The leakage resistance indicates a threshold value of a force which, in the context of this test procedure, is applied to a plunger rod introduced into the syringe body and operatively connected to the latter. The leakage resistance is defined as the highest threshold value of a force, below which leakage occurs in not more than 1.8% of the tested syringe bodies. At least 56 measurements of syringe bodies of the same configuration and design are needed in order to provide a meaningful result for the leakage resistance.

Measurement

In the test procedure for measuring the NPO resistance and the leakage resistance the syringe body to be tested is arranged vertically in a test machine and held in the region of the proximal end of the syringe body. The test machine used is a universal test machine "TesT 106.2 kN" from the company TesT. The syringe body to be tested is connected via the Luer lock connector to a needle arrangement which, in order to produce the Luer lock connection by a Luer lock connector counter piece, is screwed onto the distal end portion of the syringe body with a torque of 12 Ncm. The test procedure is intended to be carried out specifically with the needle arrangement Terumo 27 G×½", regular wall needle, ref NN-2713R. The needle arrangement used for the test procedure comprises, as Luer lock connector counter piece, an inner cone and two fins arranged on an outer circumference of a needle hub of the needle arrangement. The needle arrangement used for the test procedure comprises a cannula or hollow needle with a thickness of 27 G and a length of 0.5 in, approx. 13 mm, (27 G×½). Before the test is carried out, the cannula is, for test purposes, flattened by a hammer and thereby closed. For the test procedure, a dry Luer lock connection is to be produced by screwing the needle arrangement onto the syringe body before then the syringe is filled completely with Lipovenos® MCT 20 vol. %, available from Fresenius Kabi Deutschland GmbH. The test procedure is carried out with non-steam-sterilized components (syringe body, needle arrangement, plunger rod). After the syringe has been filled a plunger rod is introduced into the syringe body and is operatively connected to the latter, although the syringe body and the plunger rod are still in a starting position at the start of the test procedure, i.e., in a non-actuation position. For the present test procedure, a standard plunger rod is to be used that is provided for the respective syringe body to be tested.

By way of a test punch of the test machine, a force is applied vertically to a proximal end of the plunger rod. The test punch moves at a constant test speed of 12.6 mm/min in the direction of the distal end portion of the syringe body. The force acting on the plunger rod increases continuously to a maximum of 420 N. In the testing, the test punch is moved by a distance of 15 mm. The acting force is detected by a force sensor at a scanning rate of 200 Hz. The test punch is moved onwards, or the acting force increased, until leakage and/or NPO occurs, or until the maximum force of 420 N is reached. The test is stopped, i.e. leakage and/or NPO is identified, if the measured force drops suddenly by at least 30%. The acting force at the time of occurrence of leakage and/or NPO is documented and linked to the information on whether leakage and/or NPO has occurred at this force. From the documented measurement results, the previously described NPO resistance and the leakage resistance is then determined. Leakage and NPO are also referred to herein as discharge failures.

Exemplary embodiments provided according to the invention are set out in more detail below by means of examples and figures, with the examples and figures not denoting any restriction on the invention. Furthermore, unless otherwise indicated, the figures are not to scale.

Figure 2:
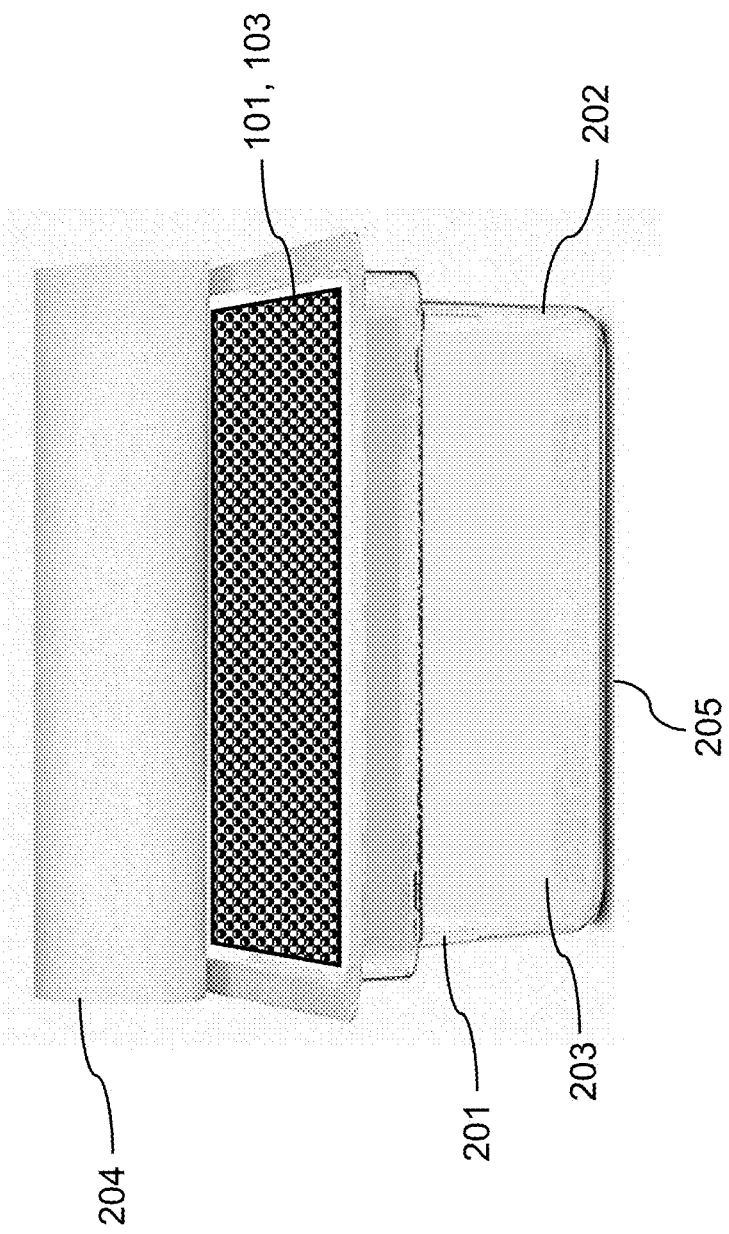
FIG. 2 illustrates a scheme of a further arrangement provided according to the invention.

For each of the examples and comparative examples, 36 commercially available polymer syringes of the type Top-Pac® 1 mL 1 g from Schott AG are loaded into a holding device, also referred to as a nest. These syringes consist of a cyclic olefin copolymer (COC). Each of the nests includes 6 rows and, perpendicular thereto, 6 columns of orifices in a base body for holding 36 syringes. The specific type of the respective nest is given in Table 1 below by reference to the figure which shows in a detail view how the syringes are held in the nest. Each of the loaded nests of the examples and comparative examples is placed into a tub as depicted in FIGS. 2 and 8. The filled tub is closed by sealing a gas-permeable lid onto the upper rim of the tub via a hotmelt.

TABLE 1

|  | Holding Device of FIG.(s) |
| --- | --- |
| Example 1 | 4A and 4B |
| Example 2 | 5A and 5B |
| Example 3 | 6A and 6B |
| Comparative Example 1 | 14 |
| Comparative Example 2 | 17 |

10 closed tubs for each example and comparative example are each subjected to the transport simulation described previously in the test methods section. Subsequently, the particle load on the exterior surfaces of the 36 syringes is determined as described previously in the test methods section. For each of the examples 1 to 3 the number of particles of particles sizes of at least 5 μm does not exceed 2.7 per cm², whereas the number of particles of particles sizes of at least 2 μm does not exceed 8.7 per cm². In the comparative examples 1 and 2, the number of particles of particles sizes of at least 5 μm is above 2.7 per cm² and the number of particles of particles sizes of at least 2 μm is above 8.7 per cm². In particular, example 3 shows a number of particles of particles sizes of at least 5 μm of 2.47 per cm² and per a number of particles of particles sizes of at least 2 μm of 6.47 cm². Comparative example 1 shows a number of particles of particles sizes of at least 5 μm of 2.77 per cm² and per a number of particles of particles sizes of at least 2 μm of 8.81 cm². The below Table 2 summarizes the results for all the examples and comparative examples. Therein, ++ means less particles than + which means still less particles than −.

TABLE 2

|  | Number of Particles of Particle Size ≥5 μm per cm² | Number of Particles of Particle Size ≥2 μm per cm² |
| --- | --- | --- |
| Example 1 | + | + |
| Example 2 | + | + |
| Example 3 | ++ | ++ |
| Comparative Example 1 | − | − |
| Comparative Example 2 | − | − |

After having been subjected to the transport simulation described previously in the test methods section, the syringes from 100 tubs of each of the examples and comparative examples are processed further in an automated manner in a standard filling machine. The tub is opened by cutting through the lid with knives and the syringes are taken out of the nest by a robotic arm. Therein, the robotic arm grips the syringes with a gripper, and moves them to the filling station by a swivel motion. The number of processing failures, in particular failures to correctly grip and withdraw the syringes from the nest and syringes which are not tightly gripped during the swivel motion, are counted for each example and comparative example.

Further 10 tubs of each of the examples and the comparative examples are subjected to the transport simulation described above in the test methods section. Subsequently, the NPO resistance and leakage resistance of 100 syringes which have arbitrarily been taken from those 10 tubs of each of the examples and the comparative examples are determined as described previously in the test methods section.

Further, after having been subjected to the transport simulation described previously in the test methods section, the syringes of 10 tubs of each of the examples and comparative examples are processed further by vacuum packaging them in plastic foil bags. The packaged containers are given in a cardboard box, which is closed and then shaken manually for 5 minutes. Subsequently, the box is opened and the foil bags are studied by naked eye and optical microscope (10-fold magnification) for damages, such as scratches, pinholes and tears.

The results of the above studies are summarized in the below Table 3. Therein, ++ indicates a result which is more favorable than +, which is still more favorable than −.

TABLE 3

|  | Processing Failures | NPO Resistance | Leakage Resistance | Low Rate of Damaged Foil Bags |
| --- | --- | --- | --- | --- |
| Example 1 | + | + | + | + |
| Example 2 | + | + | + | + |
| Example 3 | ++ | ++ | ++ | ++ |
| Comparative Example 1 | − | − | − | − |
| Comparative Example 2 | − | − | − | − |

FIG. 1 shows a scheme of an arrangement 100 provided according to the invention in cross-sectional view. This arrangement 100 comprises a holding device 101 which comprises a base body 104 and a plurality of holding elements 102 that are arranged at the at the base body 104. Further, the arrangement 100 includes a plurality of 36 containers 103. These containers 103 are syringes of the type shown in FIG. 3, however, without the plunger 311 having been applied. The base body 104 comprises a plurality of orifices 107 in a first surface 105 of the base body 104. Each of the containers 103 extends through the first surface 105 into an orifice 107 of the plurality of orifices 107. Each of the orifices 107 is an entrance to a cup which is formed by the base body 104. The holding elements 102 are arranged in the cups. Opposite the first surface 105, the base body 104 has a further surface 106. The first 105 and further surfaces 106 are plan-parallel to one another. Further, the first 105 and further surfaces 106 both extend in directions of a width and a length of the base body 104. The length of the base body 104 extends in a direction from the left to the right of the figure. In that direction, orifices 107 of the plurality of orifices 107 are arranged in rows. The width of the base body 104 extends perpendicularly to that direction, into the plane of the figure. In the latter direction, orifices 107 of the plurality of orifices 107 are arranged in columns. Altogether, the base body 104 has 36 of the orifices 107 which accommodate the 36 containers 103. Each of the containers 103 comprises a container wall 307 which partially surrounds a container interior 308 (see FIG. 3). An exterior surface of the container wall 307 faces away from the container interior 308. Further, each of the containers 103 is detachably held by a positive fit of two holding elements 102 and the exterior surface of the container wall 307 of the respective container 103. The holding elements 102 are designed as plastic clips. For details about the holding elements 102, see FIGS. 4A and 4B. After the arrangement 100 has been subjected to the transport simulation described in the test methods section, a number of particles of particles sizes of at least 5 µm does not exceed 2.7 per cm² of the sum of the surface areas of the exterior surfaces of all the containers 103 of the plurality of containers 103, whereas the number of particles of particles sizes of at least 2 µm does not exceed 8.7 per cm² of the sum of the surface areas of the exterior surfaces of all the containers 103 of the plurality of containers 103.

FIG. 2 shows a scheme of a further arrangement 100 provided according to the invention. This arrangement 100 comprises the arrangement 100 with the holding device 101 and the containers 103 of FIG. 1. Additionally, the arrangement 100 of FIG. 2 comprises a packaging container 201 which is designed as a tub. The packaging container 201 consists of a packaging container wall 202, which partially surrounds a packaging container interior 203, and a lid 204 which is sealed to an upper rim of the packaging container wall 202. The packaging container wall 202 is made from PET, whereas the lid 204 is made from a gas-permeable multilayer sheet. The packaging container 201 may be closed by completely sealing the lid 204 to the upper rim. The holding device 101 and the containers 103 are arranged in the packaging container interior 203. The packaging container 201 comprises a flat packaging container bottom 205 which is formed by the packaging container wall 202. A packaging container interior surface of the packaging container wall 202 faces the packaging container interior 203. After the arrangement 100 of FIG. 2 has been subjected to the transport simulation described in the test methods section, a number of particles of particles sizes of at least 5 µm does not exceed 2.7 per cm² of the sum of the surface areas of the exterior surfaces of all the containers 103 of the plurality of containers 103, whereas the number of particles of particles sizes of at least 2 µm does not exceed 8.7 per cm² of the sum of the surface areas of the exterior surfaces of all the containers 103 of the plurality of containers 103.

Figure 3:
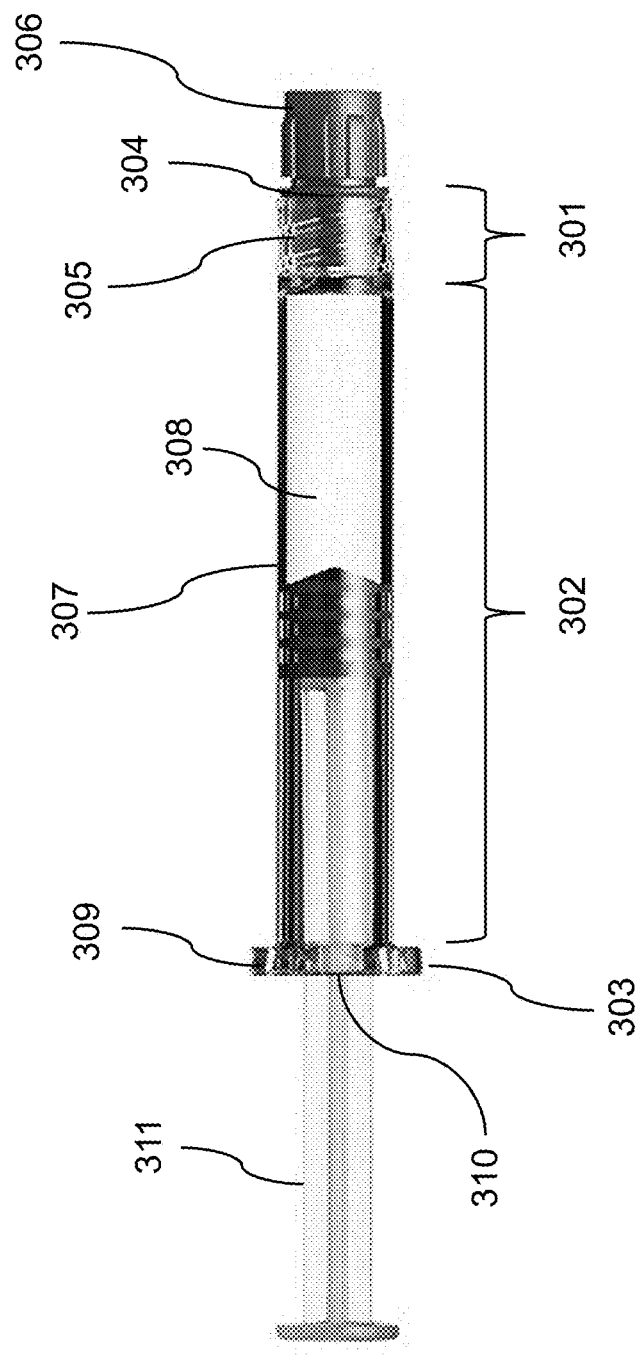
FIG. 3 illustrates a scheme of a container of an arrangement provided according to the invention.
Figure 4:
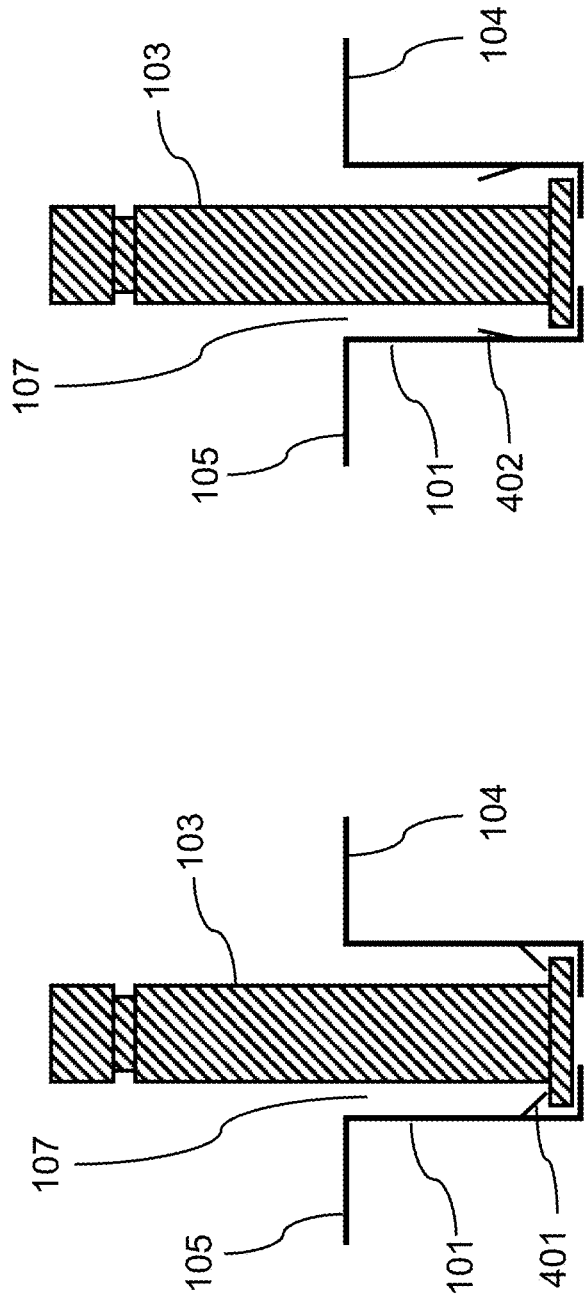
FIGS. 4A and 4B illustrate schemes of a detail of the arrangement of FIG. 1 in cross-sectional view.
Figure 5:
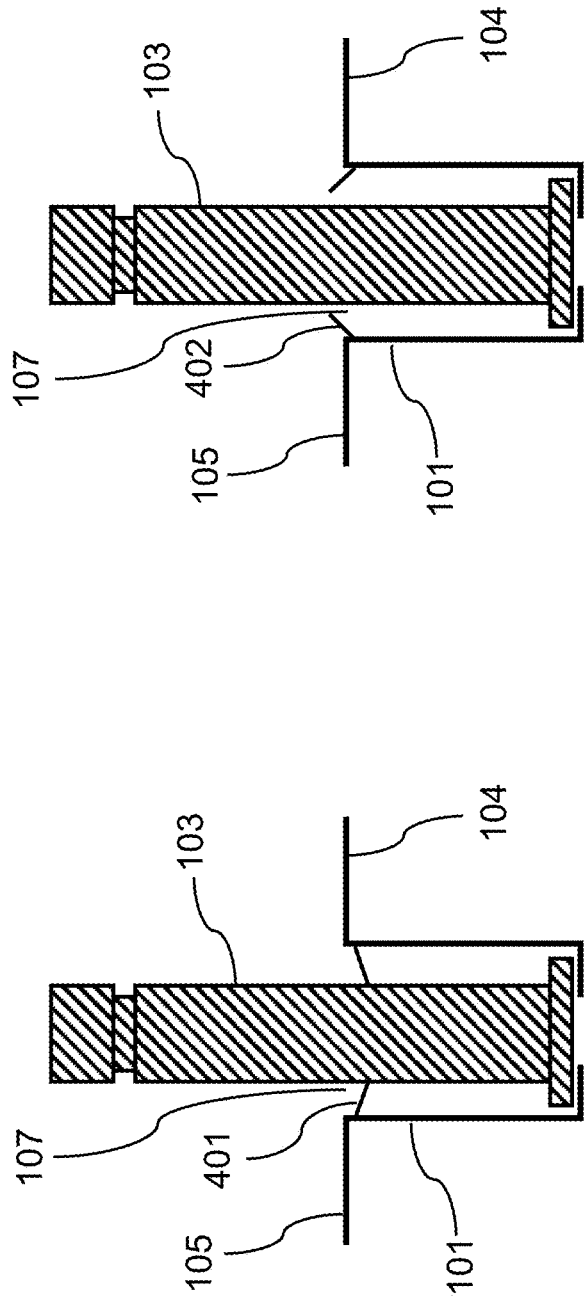
FIGS. 5A and 5B illustrate schemes of a detail of a further arrangement provided according to the invention in cross-sectional view.
Figure 6:
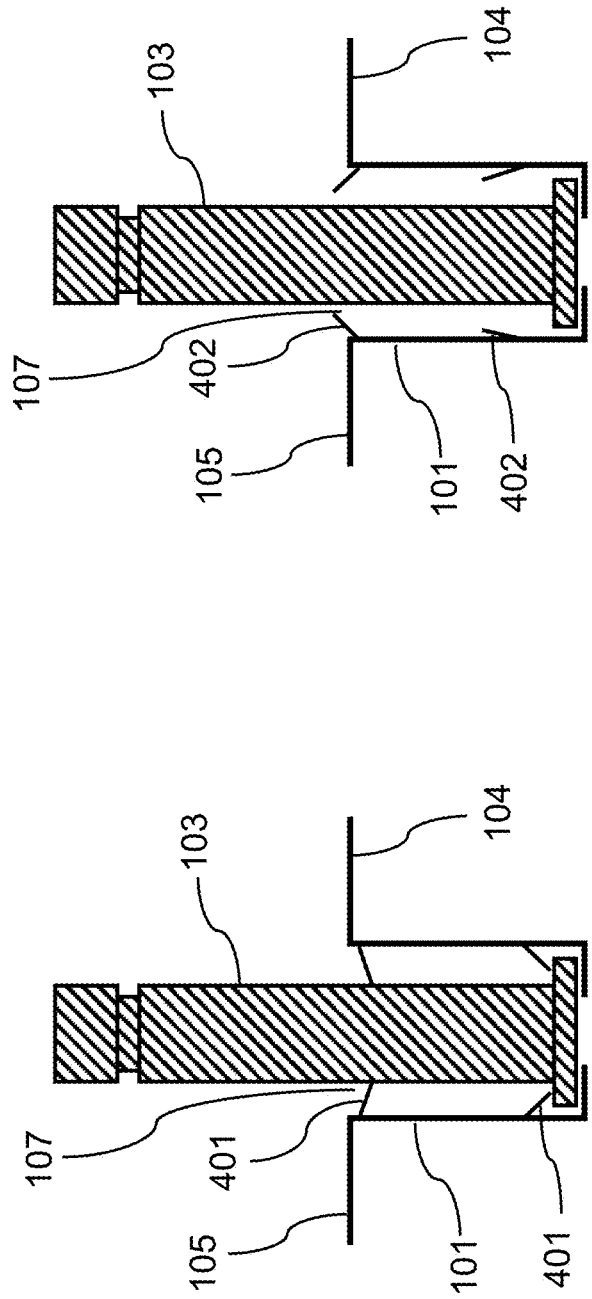
FIGS. 6A and 6B illustrate schemes of a detail of a further arrangement provided according to the invention in cross-sectional view.

FIG. 3 shows a scheme of a container 103 of an arrangement 100 provided according to the invention. The container 103 comprises a container wall 307 which partially surrounds a container interior 308. The container wall 307 forms, in the following sequence from top to bottom, a first end part 301, comprising a discharge orifice 304; a body part 302; and a further end part 303. The body part 302, which in the art is also referred to as barrel, is a hollow cylinder. The further end part 303 comprises a further orifice 310. The discharge orifice 304 has an orifice area which is less than an orifice area of the further orifice 310. The further orifice 310 accommodates a plunger 311. The further end part 303 further comprises a rim, in the art also referred to as flange, which projects laterally from beyond the body part 302 and hems the further orifice 310. The container wall 307 is made from a cyclic olefin copolymer. The first end part 301 comprises a connecting element which is a male part 305 of a Luer taper. The connecting element comprises a thread for connecting a hypodermic needle to the container 103. The thread is arranged in a sleeve. The containers 103 of the arrangement 100 of FIG. 1 are syringes of the type shown in FIG. 3, however, without the plunger 311. Further, also FIGS. 4A to 6B show the type of container 103 of FIG. 3, again without the plunger 311.

FIGS. 4A and 4B show schemes of a detail of the arrangement 100 of FIG. 1 in cross-sectional view. What is shown in each of FIGS. 4A and 4B is a container 103 which is accommodated in the same orifice 107 in the first surface 105 of the base body 104 of the holding device 101. The orifice 107 is an entrance to a cup. In FIG. 4A, the container 103 is detachably held by a positive fit of two holding elements 401 and the exterior surface of the container wall 307 of the container 103. The holding elements 401 are designed as plastic clips. In FIG. 4A, the holding elements 401 are in their holding configuration. Here, the rim of the further end part 303 of the container 103 is fixed between the holding elements 401 and a bottom of the cup. By pulling the container 103 upwards at a force which exceeds a threshold force, the clips can be elastically deformed and rotated about their connection points to the cup. That way, the holding elements 401 can be transferred from their holding configuration into a release configuration. FIG. 4B shows the holding elements 402 in the release configuration. Here, the positive fit is released and the container 103 can be withdrawn from the holding device 101. By pushing the container 103 downwards into the cup with the rim beyond the holding elements 402, the holding elements 402 can be transferred back into their holding configuration and, thus, the positive fit can be restored.

FIGS. 5A and 5B show schemes of a detail of a further arrangement 100 provided according to the invention in cross-sectional view. The arrangement 100 is identical to the arrangement 100 of FIG. 1, except for the design of the holding elements 102. Accordingly, FIGS. 5A and 5B illustrate an alternative to FIGS. 4A and 4B. What is shown in each of FIGS. 5A and 5B is a container 103 which is accommodated in the same orifice 107 in the first surface 105 of the base body 104 of the holding device 101. The orifice 107 is an entrance to a cup. In FIG. 5A, the container 103 is detachably held by two holding elements 401. The holding elements 102 are designed as plastic clips. In FIG. 4A, the holding elements 401 are in their holding configuration. Here, the holding elements 401 tightly contact the exterior surface of the container wall 307 and, thereby, hold the container 103 in place. By pulling the container 103 upwards at a force which exceeds a threshold force, the clips can be elastically deformed and rotated about their connection points to the cup. That way, the holding elements 401 can be transferred from their holding configuration into a release configuration. FIG. 4B shows the holding elements 402 in the release configuration. Here, the container 103 can be withdrawn from the holding device 101. By pushing the container 103 downwards into the cup with the rim beyond the holding elements 402, the holding elements 402 can be transferred back into their holding configuration to hold the container 103 in place again.

FIGS. 6A and 6B show schemes of a detail of a further arrangement 100 provided according to the invention in cross-sectional view. The arrangement 100 is identical to the arrangement 100 of FIG. 1, except for the design of the holding elements 102. The holding device 101 of the arrangement 100 of FIGS. 6A and 6B combines the holding elements 102 of FIGS. 4A and 4B with those of FIGS. 5A and 5B.

Figure 7:
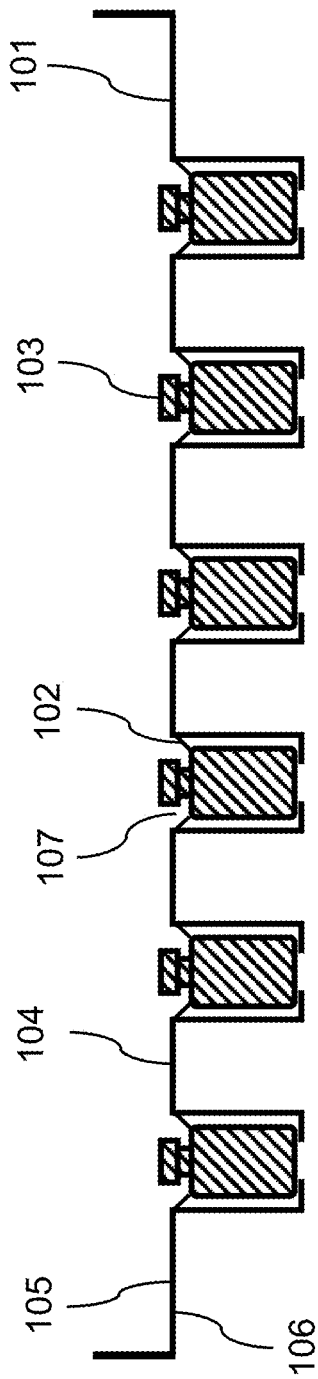
FIG. 7 illustrates a scheme of a further arrangement provided according to the invention in cross-sectional view.

FIG. 7 shows a scheme of a further arrangement 100 provided according to the invention in cross-sectional view. This arrangement 100 comprises a holding device 101 which comprises a base body 104 and a plurality of holding elements 102 that are arranged at the at the base body 104. Further, the arrangement 100 includes a plurality of 36 containers 103. These containers 103 are vials of the type shown in FIG. 9. The base body 104 comprises a plurality of orifices 107 in a first surface 105 of the base body 104. Each of the containers 103 extends through the first surface 105 into an orifice 107 of the plurality of orifices 107. Each of the orifices 107 is an entrance to a cup which is formed by the base body 104. The holding elements 102 are arranged in the cups. Opposite the first surface 105, the based body has a further surface 106. The first 105 and further surfaces 106 are plan-parallel to one another. Further, the first 105 and further surfaces 106 both extend in directions of a width and a length of the base body 104. The length of the base body 104 extends in a direction from the left to the right of the figure. In that direction, orifices 107 of the plurality of orifices 107 are arranged in rows. The width of the base body 104 extends perpendicularly to that direction, into the plane of the figure. In the latter direction, orifices 107 of the plurality of orifices 107 are arranged in columns. Altogether, the base body 104 has 36 of the orifices 107 which accommodate the 36 containers 103. Each of the containers 103 comprises a container wall 307 which partially surrounds a container interior 308 (see FIG. 9). An exterior surface of the container wall 307 faces away from the container interior 308. Further, each of the containers 103 is detachably held by a positive fit of two holding elements 102 and the exterior surface of the container wall 307 of the respective container 103. The holding elements 102 are designed as plastic clips. For details about the holding elements 102, see FIGS. 10A and 10B.

FIG. 8 shows a scheme of a further arrangement 100 provided according to the invention. This arrangement 100 is identical to that of FIG. 7, however with 4 rows and 4 columns of orifices 107 and, thus, only 25 containers 103. Additionally, the arrangement 100 of FIG. 8 comprises a packaging container 201 which is designed as a tub. The packaging container 201 consists of a packaging container wall 202 which partially surrounds a packaging container interior 203. The packaging container wall 202 is made from PET. The tub may be closed by sealing a lid 204 (not shown) to an upper rim of the packaging container wall 202. Here, the holding device 101 and the containers 103 are shown outside of the packaging container 201. This is merely for illustrative purposes. According to the invention, the holding device 101 and the containers 103 are arranged in the packaging container interior 203. The packaging container wall 202 includes a stepped projection 801 which is designed to hold the holding device 101 such that the containers 103 are positioned above a flat packaging container bottom 205 which is formed by the packaging container wall 202. A packaging container interior surface of the packaging container wall 202 faces the packaging container interior 203.

FIG. 9 shows a scheme of a container 103 of an arrangement 100 provided according to the invention. The container 103 comprises a container wall 307 which partially surrounds a container interior 308. The container wall 307 forms, in the following sequence from top to bottom, a first end part 301; a body part 302; and a further end part 303. The first end part 301 comprises a discharge orifice 304, a flange 901 and a neck 902. The flange 901 as well as the neck 901 are each of a shape of a hollow cylinder. The body part 302 follows the first end part 301 via a shoulder 903. The body part 302 is a hollow cylinder. The further end part 303 follows the body part 302 via a heel 904. In addition to the heel 904, the further end part 303 comprises a standing base 905. The container wall 307 is made from a type I glass. The containers 103 of the arrangements 100 of FIGS. 7 and 8 are vials of the type shown in FIG. 9. Further, also FIGS. 10A to 10B show the type of container 103 of FIG. 9.

FIGS. 10A and 10B show schemes of a detail of the arrangement 100 of FIG. 7 in cross-sectional view. What is shown in each of FIGS. 10A and 10B is a container 103 which is accommodated in the same orifice 107 in the first surface 105 of the base body 104 of the holding device 101. In FIG. 10A, the container 103 is detachably held by a positive fit of two holding elements 401 and the exterior surface of the container wall 307 of the container 103. The holding elements 401 are designed as plastic clips. In FIG. 10A, the holding elements 401 are in their holding configuration. Here, the shoulder 903 of the container 103 (see FIG. 9) is fixed between the holding elements 401 and a bottom of the cup. By pulling the container 103 upwards at a force which exceeds a threshold force, the clips can be elastically deformed and rotated about their connection points to the cup. That way, the holding elements 401 can be transferred from their holding configuration into a release configuration. FIG. 10B shows the holding elements 402 in the release configuration. Here, the positive fit is released and the container 103 can be withdrawn from the holding device 101. By pushing the container 103 downwards to the bottom of the cup, the holding elements 402 can be transferred back into their holding configuration and, thus, the positive fit can be restored.

FIG. 11 shows a flow chart of a process 1100 provided according to the invention for preparing the arrangement 100 of FIG. 2. In a process step A) 1101, the holding device 101, the plurality of containers 103, the packaging container 201 and the lid 204 described in the context of FIG. 2 are provided. Subsequently, in a process step B) 1102, the 36 containers 103 are loaded into the holding device 102 by inserting each container 103 into one of the cups via the orifices 107. Thereby, the holding elements 102 are transferred from their release configuration to their holding configuration such that each container 103 is detachably held by contact of two holding elements 102 to the exterior surface of the container wall 307 of the respective container 103. In a process step C) 1103, the holding device 101 with the containers 103 is placed into the packaging container 201. In a subsequent process step D) 1104, the packaging container 201 is closed by heat sealing the lid 204 to the rim of the packaging container wall 202 via a hotmelt. The arrangement 100 of FIG. 2 may be further processed in process steps E) 1105 and F) 1106 by placing the packaging container 201 with the holding device 101 and the containers 103 into an outer packaging, and closing the outer packaging. Here, the outer packaging may be a plastic bag which is heat sealed for closing.

Figure 12:
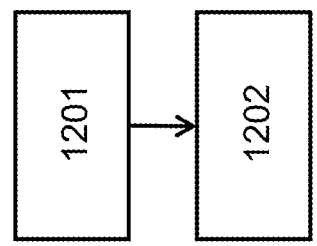
FIG. 12 illustrates a flow chart of a process provided according to the invention which includes filling containers with pharmaceutical composition.

FIG. 12 shows a flow chart of a process 1200 provided according to the invention. This process 1200 includes a process step A. 1201 of providing the arrangement 100 of FIG. 7. Further, in a process step B. 1202 each of the 36 containers 103 is filled with a pharmaceutical composition.

Figure 13:
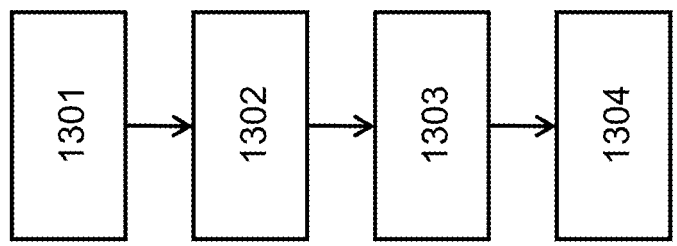
FIG. 13 illustrates a flow chart of a process provided according to the invention which includes shaking an arrangement provided according to the invention and determining particle load.

FIG. 13 shows a flow chart of a further process 1300 provided according to the invention. In a process step A], the arrangement 100 of FIG. 2 is provided with the tub closed by the lid 204. In a process step B] 1302, the arrangement 100 is subjected to the transport simulation which is described in the test methods section. In a subsequent process step C] 1303, for at least part of the containers 103 of the plurality of containers 103 the number of particles of particle sizes of at least 5 µm and of at least 2 µm are determined as described in the previous test methods section. If the number of particles of particle sizes of at least 5 µm would be above 2.7 particles per cm$^2$ or the number of particles of particle sizes of at least 2 µm would be above 8.7 particles per cm$^2$, the containers 103 would be discarded in a process step D] 1304. For the arrangement 100 of FIG. 2, this is, however, not the case. Therefore, the containers 103 are, instead, filled with a pharmaceutical composition in the process step D] 1304.

Figure 14:
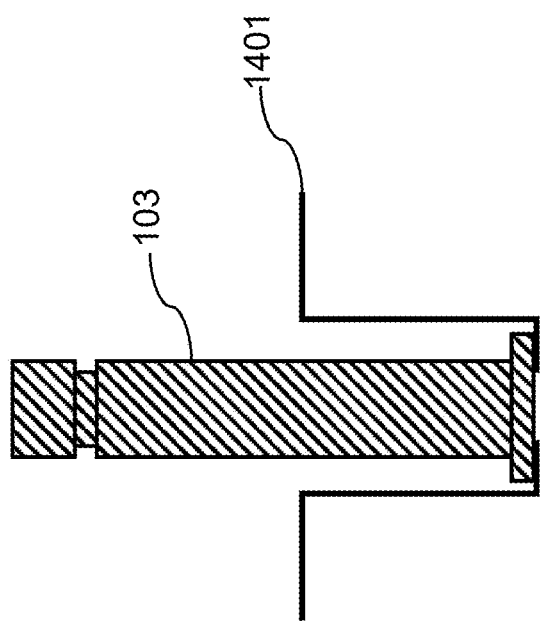
FIG. 14 illustrates a scheme of a detail of a nest not provided according to the invention.

FIG. 14 shows a scheme of a detail of an arrangement 1400 not provided according to the invention. The arrangement 1400 comprises a holding device 1401 and the plurality of 36 containers 103 described in the context of FIG. 1. Further, the holding device 1401 is designed as the holding device 101 of FIG. 1, however, without the holding elements 102. Accordingly, 36 containers 103 (syringes) are each accommodated in a cup.

Figure 15:
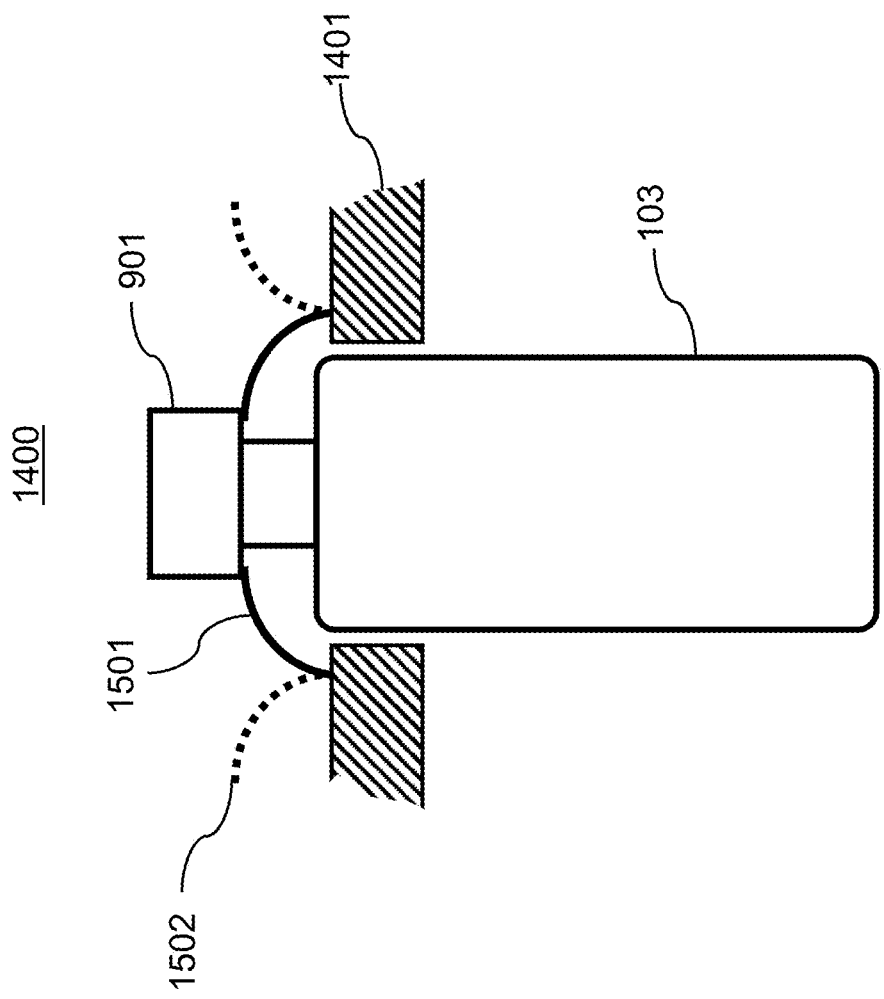
FIG. 15 illustrates a scheme of a detail of a further nest not provided according to the invention.

FIG. 15 shows a scheme of a detail of a further arrangement 1400 not provided according to the invention. The arrangement 1400 comprises a holding device 1401 and the plurality of 36 containers 103 described in the context of FIG. 7. The holding device 1401 is a so-called clip-nest which is known in the prior art. This nest comprises 36 instances of the detail shown in the FIG. 15. The clip-nest includes resilient holding arms, referred to as clips. The nest includes 2 clips per container 103 to be held. The figure shows two closed clips 1501 in holding configuration by full lines. The same clips are depicted as opened clips 1502 in opened configuration by broken lines. The clips can be snapped from the holding configuration to the opened configuration by elastically deforming the clips which are made from a plastic.

Figure 16:
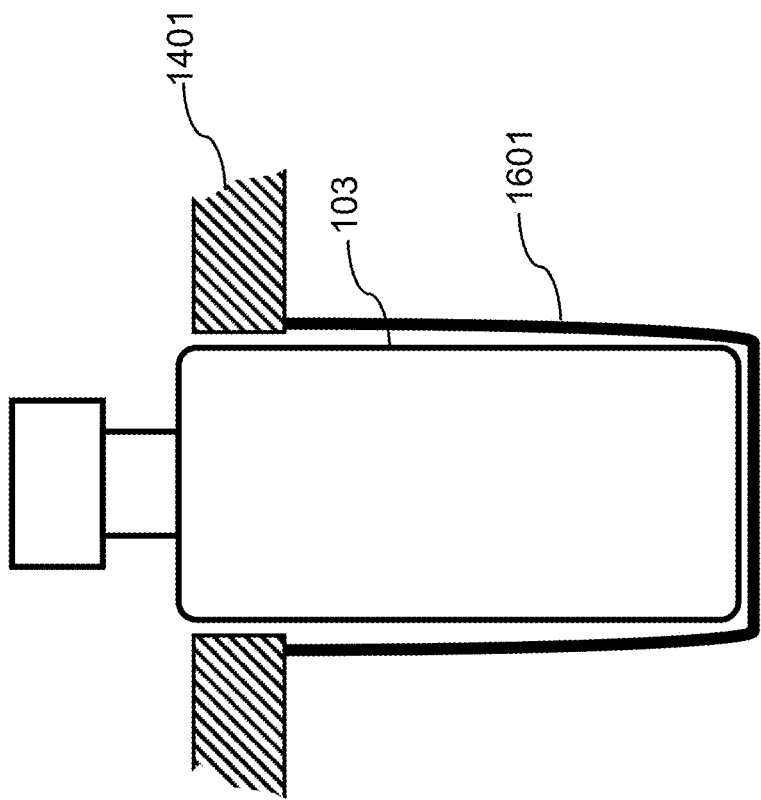
FIG. 16 illustrates a scheme of a detail of a further nest not provided according to the invention.

FIG. 16 shows a scheme of a detail of a further arrangement 1400 not provided according to the invention. The arrangement 1400 comprises a holding device 1401 and the plurality of 36 containers 103 described in the context of FIG. 7. The holding device 1401 is a so-called cup-nest which is known in the prior art. This nest comprises 36 instances of the detail shown in the FIG. 16. Accordingly, 36 orifices of the nest entrances to receptables, referred to as cups 1601. In order for the nest to hold the containers 103, each container 103 is introduced into one of the cups 1601.

Figure 17:
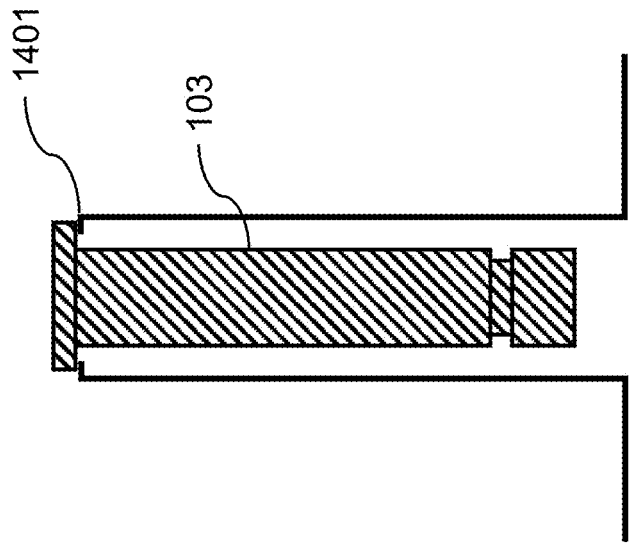
FIG. 17 illustrates a scheme of a detail of a further nest not provided according to the invention.

FIG. 17 shows a scheme of a detail of a further arrangement 1400 not provided according to the invention. The arrangement 1400 comprises a holding device 1401 and the plurality of 36 containers 103 which are syringes. The syringes are held by receptacles of the holding device 1401 in a hanging upside-down orientation.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 100 arrangement provided according to the invention
101 holding device
102 holding element
103 container
104 base body
105 first surface
106 further surface
107 orifice
201 packaging container
202 packaging container wall
203 packaging container interior
204 lid
205 packaging container bottom
301 first end part
302 body part
303 further end part
304 discharge orifice
305 male part of Luer taper
306 stopper
307 container wall
308 container interior
309 rim
310 further orifice
311 plunger
401 holding element in holding configuration
402 holding element in release configuration
801 Stepped projection
901 flange
902 neck
903 shoulder
904 heel
905 standing base
1100 process provided according to the invention for preparing arrangement provided according to the invention
1101 process step A)
1102 process step B)
1103 process step C)
1104 process step D)
1105 process step E)
1106 process step F)
1200 process provided according to the invention which includes filling containers with pharmaceutical composition
1201 process step A.
1202 process step B.
1300 process provided according to the invention which includes shaking arrangement provided according to the invention and determining particle load
1301 process step A]
1302 process step B]
1303 process step C]
1304 process step D]
1400 detail of arrangement not provided according to the invention 1401 holding device not provided according to the invention
1501 closed clip
1502 opened clip
1601 cup

What is claimed is:

1. An arrangement, comprising:
a holding device comprising a plurality of holding elements; and
a plurality of containers, each of the containers of the plurality of containers comprising a container wall which at least partially surrounds a container interior, the container wall having an exterior surface which faces away from the container interior, each of the containers of the plurality of containers being detachably held by at least one of the holding elements by contact of the at least one holding element to the exterior surface of the container wall of the respective container of the plurality of containers, wherein, directly after the arrangement has been subjected to a transport simulation, a number of particles of a particle size of at least 5 μm on the exterior surfaces of the containers of the plurality of containers does not exceed 2.7 particles per cm² of a sum of surface areas of the exterior surfaces of all the containers of the plurality of containers, the transport simulation consisting of a rotational flat drop test and a random vibration test which are conducted subsequently in that order.

2. The arrangement of claim 1, wherein the number of particles of a particle size of at least 2 μm on the exterior surfaces of the containers of the plurality of containers does not exceed 8.7 particles per cm² of the sum of the surface areas of the exterior surfaces of all the containers of the plurality of containers.

3. The arrangement of claim 1, wherein the holding device comprises at least one base body, the at least one base body comprising the holding elements or the holding elements of the plurality of holding elements are arranged at the at least one base body.

4. The arrangement of claim 3, wherein the at least one base body comprises a plurality of orifices in a first surface, wherein each of the containers of the plurality of containers extends at least through the first surface into an orifice of the plurality of orifices.

5. The arrangement of claim 1, wherein each of the containers of the plurality of containers is detachably held by a positive fit, a frictional fit, or a combination of both of at least one holding element and the exterior surface of the container wall of the respective container of the plurality of containers.

6. The arrangement of claim 1, further comprising a packaging container comprising a packaging container wall which at least partially surrounds a packaging container interior, wherein the holding device and the containers are arranged in the packaging container interior.

7. The arrangement of claim 6, wherein at least one of the following is satisfied:
the packaging container is closed by a lid which is joined to the packaging container;
the arrangement further comprises an outer packaging, wherein the packaging container is arranged in the outer packaging; or
the containers have been at least one of decontaminated or sterilized.

8. The arrangement of claim 7, wherein the arrangement comprises a closed outer packaging.

9. The arrangement of claim 8, wherein the outer packaging comprises a bag that is heat sealed.

10. The arrangement of claim 1, wherein the containers of the plurality of containers are packaging containers for a pharmaceutical packaging good, a cosmetical packaging good, or both.

11. The arrangement of claim 1, wherein each of the containers of the plurality of containers comprises, in the following sequence:
a first end part comprising a discharge orifice;
a body part; and
a further end part.

12. The arrangement of claim 11, further comprising a packaging container, wherein the further end parts of the containers of the plurality of containers face a bottom of the packaging container.

13. The arrangement of claim 1, wherein the containers are selected from the group consisting of vials, syringes, cartridges, ampoules, and a combination of at least two thereof.

14. The arrangement of claim 1, wherein, for each of the containers of the plurality of containers, the container wall comprises a glass, a polymer, or both.

15. The arrangement of claim 14, wherein the container wall comprises a polymer, wherein the polymer is a cyclic olefin copolymer, a cycloolefin polymer, or a mixture thereof.

16. The arrangement of claim 14, wherein the container wall comprises a glass, wherein the glass is of a type selected from the group consisting of a borosilicate glass, a type I glass, an aluminosilicate glass, fused silica, and a combination of at least two thereof.

17. The arrangement of claim 1, wherein at least some of the containers of the plurality of containers contain a pharmaceutical packaging good, a cosmetical packaging good, or both.

18. The arrangement of claim 1, wherein each of the holding elements is movable between a holding configuration and a release configuration, each of the holding elements contacting the exterior surface of a respective one of the containers in the holding configuration and being out of contact with the exterior surface of the respective container in the release configuration.

19. The arrangement of claim 18, wherein each container is contacted by a respective plurality of holding elements in the holding configuration, the holding elements being elastically deformable between the holding configuration and the release configuration by movement of the respective container.

* * * * *